United States Patent [19]

Goldstein

[11] Patent Number: 5,073,482
[45] Date of Patent: Dec. 17, 1991

[54] ELASTIC BARRIER PERMEABILITY TESTING DEVICE AND METHOD OF USE

[75] Inventor: Andrew S. Goldstein, Portland, Oreg.

[73] Assignee: Epitope, Inc., Beaverton, Oreg.

[21] Appl. No.: 209,373

[22] Filed: Jun. 21, 1988

[51] Int. Cl.⁵ .................. C12Q 1/70; G01N 15/08; G01M 3/02

[52] U.S. Cl. .................. 435/5; 422/301; 436/2; 436/3; 73/38; 73/40; 73/865.3

[58] Field of Search ............. 435/5, 31, 311; 436/1, 436/2, 3; 73/40, 41.2, 46, 47, 38, 865.3, 866, 862.39, 862.62, 838, 64.3; 210/321.65; 422/301

[56] References Cited

U.S. PATENT DOCUMENTS

| | | | |
|---|---|---|---|
| Re. 30,410 | 10/1980 | Povlacs | 406/87 |
| 3,992,766 | 11/1976 | Field | 29/235 |
| 4,492,116 | 1/1985 | Gillier et al. | 73/432 R |
| 4,538,460 | 9/1985 | Schetter, Jr. | 73/432 R |
| 4,586,376 | 5/1986 | Outmans | 73/432 R |
| 4,594,884 | 6/1986 | Bondi et al. | 73/64.3 |
| 4,667,504 | 5/1987 | Hobson | 73/38 |
| 4,719,809 | 1/1988 | Johanson et al. | 73/866 |
| 4,812,407 | 3/1989 | Buchmann et al. | 436/291 |
| 4,839,280 | 6/1989 | Banes | 435/285 |

FOREIGN PATENT DOCUMENTS 1144493   11/1986   U.S.S.R.

*Primary Examiner*—David L. Lacey
*Assistant Examiner*—Janelle D. Waack
*Attorney, Agent, or Firm*—Wegner, Cantor, Mueller & Player

[57] ABSTRACT

A device for testing an elastic membrane for permeability ot submicroscopic particles. The device has a first chamber to contain the particles in a fluid medium; a second chamber to contain a reagent for detecting the presence of any of the particles; suitable structure for mounting the membrane between the chambers in a fluid-tight manner so that the membrane separates the chambers; and a mechanism for applying stress to the membrane.

32 Claims, 3 Drawing Sheets

5,073,482

ELASTIC BARRIER PERMEABILITY TESTING DEVICE AND METHOD OF USE

BACKGROUND OF THE INVENTION

This invention relates to testing elastic barriers for permeability to microscopic particles. In particular, this invention relates to testing such barriers used in the prevention of disease transmission.

Barrier membranes made of elastic material have been used to prevent the transmission of microorganisms and the diseases they cause. Well known examples of such use are surgical gloves and condoms, both typically made of latex rubber. Originally developed as a means of preventing pregnancy, condoms have become increasingly important in preventing the spread of sexually transmitted diseases, especially the recently discovered acquired immune deficiency syndrome, commonly known as AIDS.

In this regard, typical membranes having a pore size between $0.1$ and $0.4\mu$ have been shown effective in blocking microorganisms such as bacteria and fungi. However, the efficacy of such barriers is questionable with respect to virus-caused diseases, such as AIDS, which often have particle diameters less than $0.1\mu$. Accordingly, the importance of membrane-permeability testing has become increasingly important with the awareness of diseases caused by viruses.

Few studies have been conducted to test barrier membrane permeability to viruses. In one such study, condom permeability was tested by merely immersing a condom containing a liquid suspension of a virus in a liquid growth medium for the virus, and assessing viral appearance in the growth medium (see Abstracts of the III International Conference on AIDS, Washington, D.C., 1987).

However, in actual use, elastic barrier membranes are frequently subjected to stretching and abrasion, sometimes over extended periods of time. For example, surgical gloves may be subjected to different stretching parameters depending on the size of the user's fingers, the frequency and force of finger movement required, and the abrasiveness of the material encountered during a particular session, the duration of which often varies depending upon surgical skill. Such stresses may adversely affect the original pore size of the barrier, i.e., a barrier originally impermeable to a small particle may dramatically lose its impermeability properties both during and after stretching.

SUMMARY OF THE INVENTION

It is therefore, a primary object of the present invention to provide a device and method for testing elastic membranes which is free of the aforementioned and other such disadvantages.

Another object of the present invention to develop a device and method for testing elastic membranes for permeability to microscopic particles, particularly microorganisms, under controlled conditions of simulated use that are easy to use and are easily sterilized.

According to the present invention a device for testing an elastic membrane for permeability to submicroscopic particles comprises: (a) means defining a first chamber to contain the particles in a fluid medium; (b) means defining a second chamber to contain a reagent for detecting the presence of any of said particles; (c) means for mounting said membrane between said chambers in a fluid-tight manner whereby said membrane separates said chambers; and (d) means for applying stress to said membrane. Also according to the present invention, a method for testing an elastic membrane for permeability to submicroscopic particles comprises the steps of: (a) interposing said membrane between (i) said particles in a fluid medium and (ii) a reagent for detecting the presence of said particles; and (b) applying stress to said membrane.

DESCRIPTION OF THE PREFERRED EMBODIMENTS

The invention itself, as well as additional advantages and features thereof, will be more readily and comprehensively understood from the following detailed description of the preferred inventive embodiments, such description making reference to the appended sheets of drawings, wherein:

Consistent with the foregoing objects, the preferred embodiments of the instant invention are an apparatus and method for evaluating barrier permeability properties of elastic barrier membranes. Three basic parameters of stretching, i.e., force applied, extent of barrier distortion, and frequency of barrier stretching, are precisely defined and evaluated to determine whether a particular barrier is capable of preventing microbial or chemical penetration under a given set of conditions.

Figure 1:
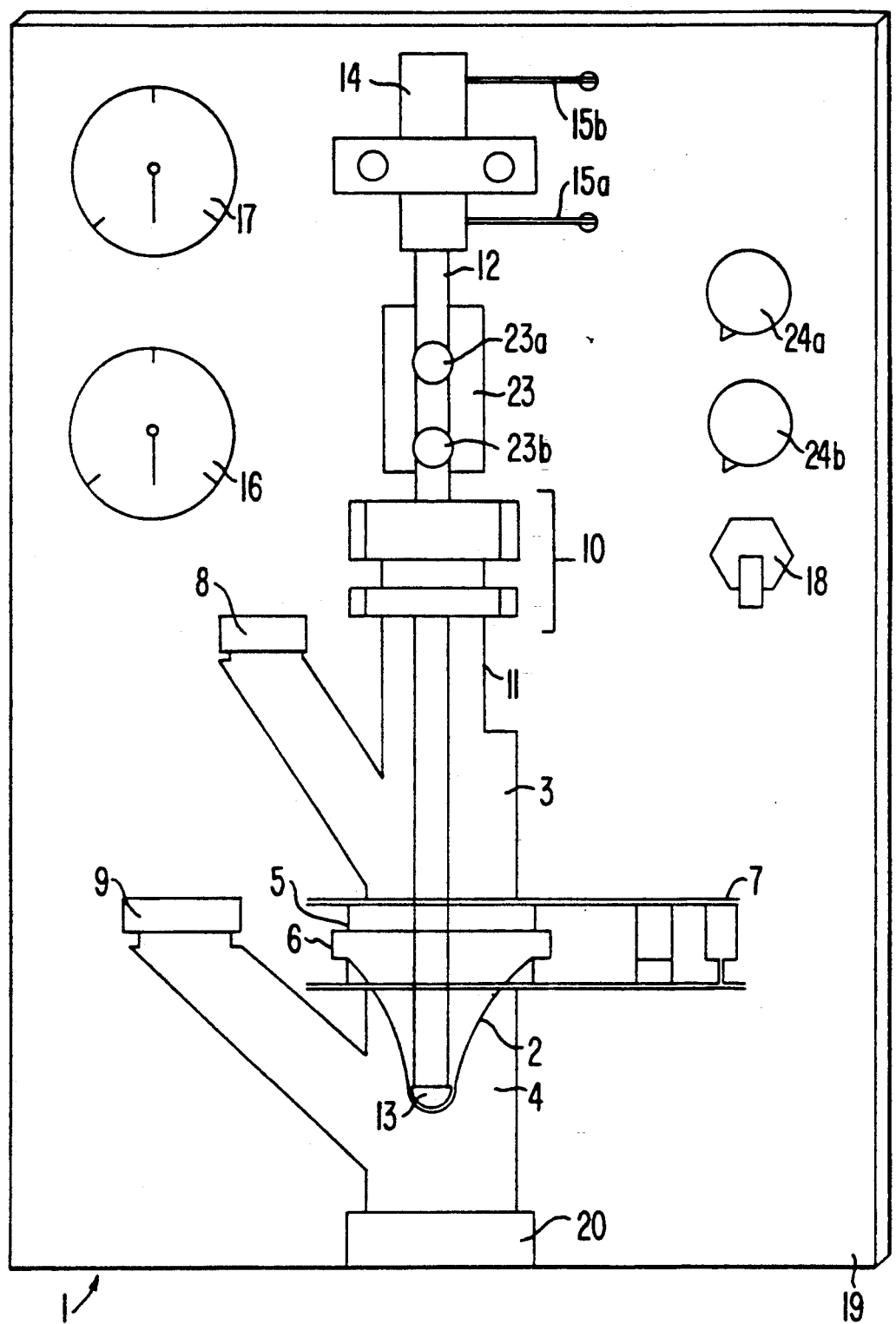
FIG. 1 is a schematic front elevational view of an automated testing device according to the present invention.
Figure 2:
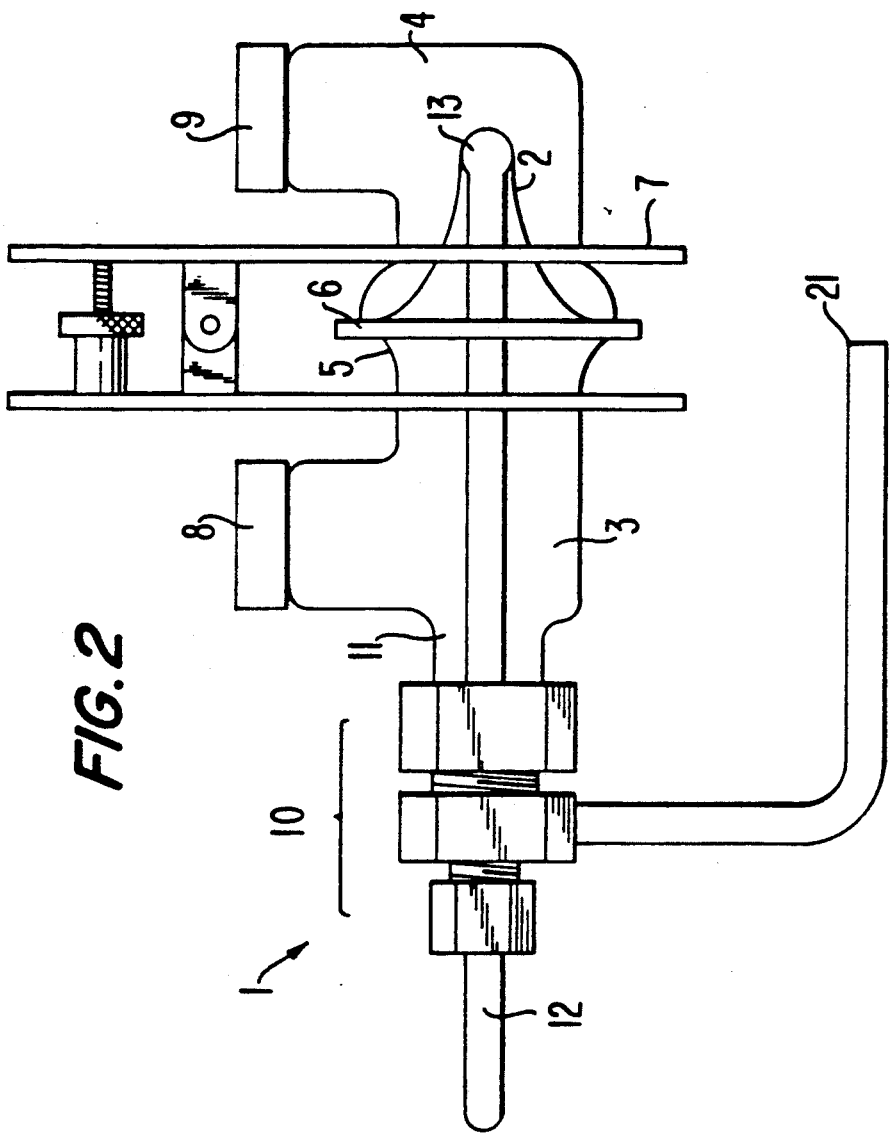
FIG. 2 is a schematic front elevational view of a manually operated embodiment.

Attention is directed to FIGS. 1 and 2, which depict a specially constructed dual chamber device generally designated by the numeral 1 which evaluates the ability of an elastic barrier 2 to prevent HIV virus (or other microscopic particle) in chamber 4 from penetrating the barrier and infecting a permissive T-cell line (or other reagent) located in chamber 3. Barrier 2 is fixed between ball extension 5 of chamber 3 and socket extension 6 of chamber 4 by means of clamp 7. Reagent and particles can be inserted into their respective chambers through closable openings 8 and 9. Fitting 10 seals neck 11 of chamber 3, through which a piston 12 enters the chamber. Rounded end 13 of piston 12 is shown stretching barrier 2.

Figure 3:
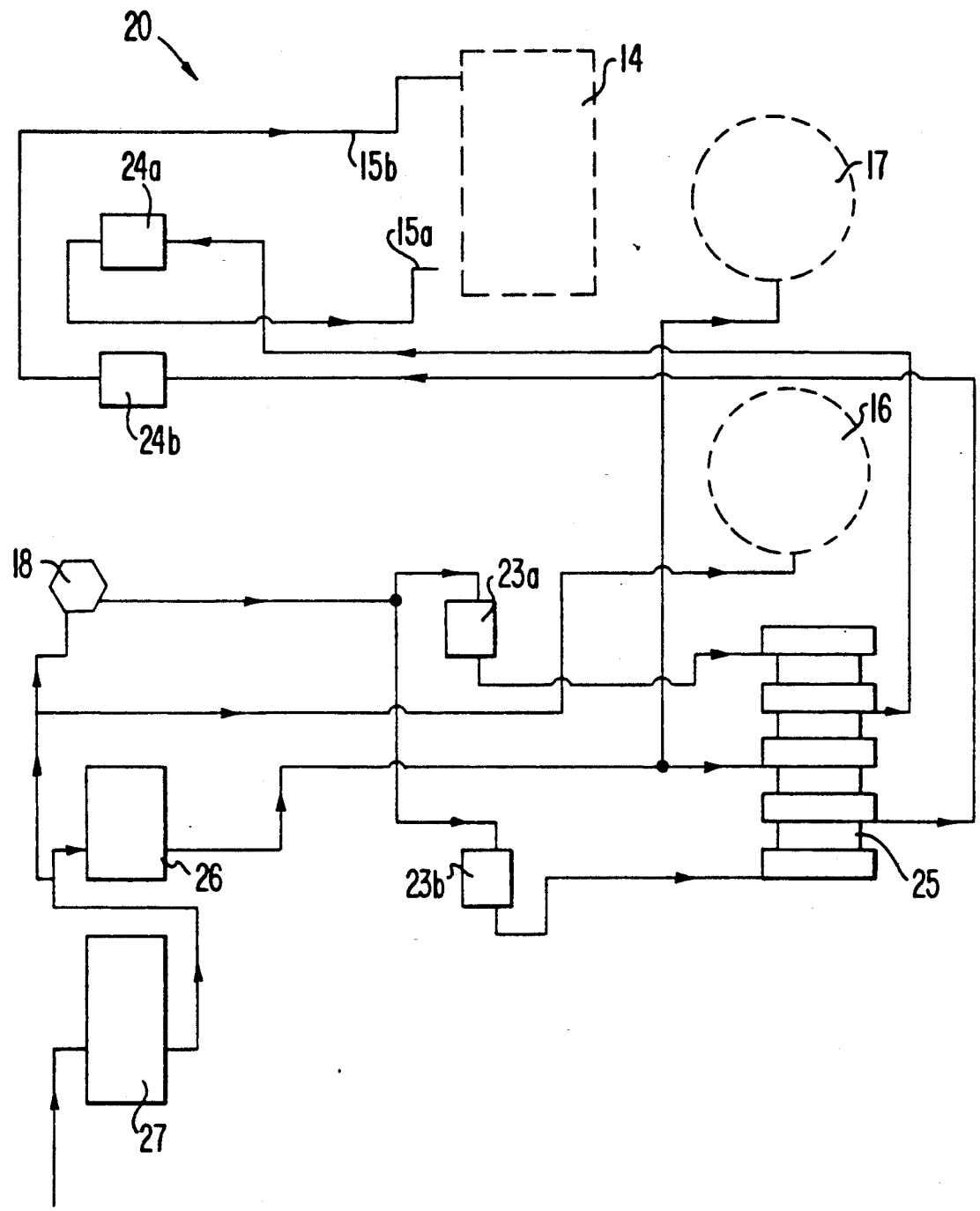
FIG. 3 is a schematic representation of a means for controlling the embodiment shown in FIG. 1.

FIGS. 1 and 3 depict an automated embodiment of the present invention and its control means. In FIG. 1, piston 12 is a smooth, stainless steel rod driven by pneumatic solenoid 14 such as model PD7-03.1 AT manufactured by Airmatic-Allied, Inc. using air from compressor (not shown) directed through control means 28. Dual mount stand 19 supports the device in a vertical position through support 20, which forms a seat for chamber 4, and through fixed attachment to fitting 10, as well as other components for the automated embodiment. It will be understood that any suitable support may be used, and that the device may be supported in a horizontal position. On/off valve 18 controls operation of the automated device.

Piston force, travel distance, and movement frequency are controlled via means 28. Air from compressor (not shown) enters control means 28 through filter/air pressure regulator 27. Incoming air pressure is monitored by main psi gauge 16. Air pressure entering solenoid 14 through lines 15a and 15b is controlled by solenoid pressure regulator 26 and monitored by solenoid psi gauge 17. Logic module 25 directs air flow (arrows) to pre-set down stroke-rate control valve 24a or pre-set up stroke-rate control valve 24b based on a pneumatic signal from either pre-set down stroke-length control valve 23a or pre-set up stroke-length control valve 23b, which are pressure venting switches triggered by motion of piston 12. These two pressure/-venting switches alternately pressurize and vent the solenoid on either side of the piston under control of the logic module, thereby creating an up and down stroke.

In FIG. 2, piston 12 is a glass rod that is operated by hand (not shown). Single mount stand 21 supports the device in a horizontal position through fixed attachment to fitting 10. Again it will be understood that the device may be supported by any suitable means, and may be vertical.

Preferably, chambers 3 and 4 are made of a heat-tempered glass material, such as Pyrex TM or any other suitable sterilizable material such as stainless steel, with closable openings 8 and 9 preferably comprising threaded spouts covered with plastic screw caps. Any elastic membrane material, e.g., latex, silicone, vinyl, polyurethane, or any other suitable elastomeric material, can be tested according to the present invention.

The present invention is useful for testing permeability to viruses, such as HIV, herpes, Epstein Barr, and hepatitis, and bacteria, such as *Treponema pallidum*, as well as fungi, protozoa, DNA molecules, RNA molecules, proteins, and other toxic or infectious agents.

The following non-limiting examples are presented to more clearly describe the present invention. Any parts and percentages therein are by weight, unless indicated otherwise.

EXAMPLE 1

Chamber parts, fittings and steel piston are thoroughly cleaned using a tissue culture grade detergent followed by five rinses in deionized water. Each cleaned component is then packaged in autoclave bags and steam sterilized at 121° C. for 30 minutes. The device is assembled in a laminar flow hood using sterile gloves.

A latex rubber condom is placed over the ball extension (5) without stretching the material. The ball-and-socket joint separating the two chambers is clamped together and the remaining parts assembled in a vertical position as shown in FIG. 1.

The upper chamber of the device is filled with a CEM cell line (T-cell lymphoma-ATCC #TiB-195) suspension of one million cells per ml of medium comprising RPMI 1640, 15% fetal calf serum, and Pen/-Strep, which permits growth of HIV virus. The cells are allowed to settle on the membrane. At least the remaining steps are performed in a suitable isolated environment such as a laminar flow hood. It is preferred that all steps be performed in the laminar flow hood while wearing sterile gloves.

The lower chamber is filled with freshly harvested HIV virus suspended in tissue culture medium at a concentration of 10 million infectious units per ml. The medium contains RPMI 1640, 15% fetal calf serum, 2 mM L-glutamine, Boehringer-Mannheim Nutridoma—HU, and Pen/Strep (Irving Scientific).

The piston is set to automatically exert up to 25 psi against the membrane for a distance of up to 3 inches (73.5 mm), at a rate of up to 3 cycles per second for 5 minutes to 4 hours, while the temperature is maintained at about 37° C.

The CEM cell line suspension is then removed from the upper chamber and placed in tissue culture medium. After culturing for 28 days, the medium is assayed for the production of viral core antigen by antigen capture as well as staining of infected cells by anti-HIV monoclonal antibodies every 4 days.

EXAMPLE 2

The procedure of Example 1 is repeated except that the HIV-containing suspension is placed in the upper chamber and the CEM cell line is placed in the lower chamber.

It will be appreciated by those skilled in the art that the device of the instant invention can be used to test porosity of a membrane to any particle even of molecular size. For instance, if a solution of an acid is filled into chamber 4 and an indicator such as methyl orange as the reagent is placed in chamber 3, a membrane can be tested for porosity to the hydrogen ion.

It should now be apparent that the objects initially set forth at the outset to this specification have been successfully achieved. Moreover, while there is shown and described present preferred embodiments of the invention, it is to be distinctly understood that the invention is not limited thereto, but may be otherwise variously embodied and practiced within the scope of the following claims.

What is claimed is:

1. A device for testing an elastic membrane for permeability to particles comprising: (a) means defining a first chamber to contain the particles in a fluid medium; (b) means defining a second chamber to contain a reagent for detecting the presence of any of the particles; (c) means for mounting the membrane between said chambers in a fluid-tight manner whereby the membrane separates said chambers; and (d) means for repeatedly applying mechanical stress to the membrane as mounted, such that the membrane is alternately stretched and released to the original position.

2. The device of claim 1, wherein said means defining a first chamber has a closable opening for receiving the particles in a fluid medium.

3. The device according to claim 2, wherein said means defining a second chamber has another opening positioned and arranged so as to be movably engaged by said means for applying stress.

4. The device of claim 2, wherein said means defining a first chamber comprises heat-tempered glass.

5. The device of claim 1, wherein said means defining a second chamber has a closable opening for receiving said reagent.

6. The device according to claim 5, wherein said means defining a second chamber has another opening positioned and arranged so as to be movably engaged by said means for applying stress.

7. The device of claim 5, wherein said means defining a second chamber comprises heat-tempered glass.

8. The device of claim 1, wherein said means for mounting comprises a ball-and-socket joint having a window therethrough, the ball of which extends from one of said means defining a first chamber and a second chamber and the socket of which extends from the other, held together by a clamping means, such that the membrane will be fixed between the ball and socket closing the window.

9. The device of claim 1, further comprising an elastic membrane to be tested, mounted in said mounting means, wherein the membrane is a latex material.

10. The device of claim 1, further comprising an elastic membrane to be tested, mounted in said mounting means, wherein the membrane is a silicone material.

11. The device of claim 1, further comprising an elastic membrane to be tested, mounted in said mounting means, wherein the membrane is a vinyl material.

12. The device of claim 1, further comprising an elastic membrane to be tested, mounted in said mounting means, wherein the membrane is a polyurethane material.

13. The device of claim 1, wherein said means for applying stress comprises a piston movably disposed along an axis, such that a rounded end of said piston can engage and stretch the membrane.

14. The device of claim 13, wherein said piston is a pneumatically driven smooth, stainless steel rod.

15. The device of claim 1, further comprising an elastic membrane to be tested, mounted in said mounting means, wherein said membrane comprises a condom.

16. The device of claim 1, further comprising an elastic membrane to be tested, mounted in said mounting means, wherein said membrane comprises a surgical glove.

17. A method for testing an elastic membrane for permeability to particles comprising the steps of: (a) interposing the membrane between (i) said particles in a fluid medium and (ii) a reagent for detecting the presence of said particles; (b) repeatedly applying mechanical stress to the membrane as interposed, such that the membrane is alternately stretched and released to its original position; and (c) determining whether any of said particles passed through the membrane.

18. The method of claim 17, wherein said membrane is fixed in a fluid-tight manner between (i) means defining a first chamber containing said particles in said fluid medium and (ii) means defining a second chamber containing said reagent, whereby said membrane separates said chambers.

19. The method of claim 18, wherein the membrane is fixed in a fluid-tight manner by a ball-and-socket joint held together by a clamping means and having a window therethrough, the ball of which extends from one of said means defining a first chamber and a second chamber, and the socket of which extends from the other of said means defining a first chamber and a second chamber, such that the membrane is fixed between the ball and socket closing the window.

20. The method of claim 17, wherein the membrane is a latex material.

21. The method of claim 17, wherein the membrane is a silicone material.

22. The method of claim 17, wherein the membrane is a vinyl material.

23. The method of claim 17, wherein the membrane is a polyurethane material.

24. The method of claim 18, wherein said stress is applied to said membrane by means of a piston moving along a longitudinal axis substantially normal to said membrane through said means defining a second chamber, such that a rounded end of said piston engages said membrane applying pressure thereto.

25. The method of claim 17, wherein said particles comprise living microorganisms.

26. The method of claim 25, wherein said reagent comprises liquid tissue culture medium.

27. The method of claim 25, wherein said particles are viruses, bacteria, fungi, or protozoa.

28. The method of claim 27, wherein said particles are HIV viruses.

29. The method of claim 17, wherein said stress is applied by a piston moving along a longitudinal axis substantially normal to said membrane, such that a rounded end of said piston engages and stretches said membrane.

30. The method of claim 29, wherein said piston is a pneumatically driven steel rod.

31. The method of claim 17, wherein said membrane is a condom.

32. The method of claim 17, wherein said membrane is a surgical glove.

* * * * *